United States Patent [19]

Garbrecht et al.

[11] Patent Number: 4,782,063

[45] Date of Patent: Nov. 1, 1988

[54] ERGOLINE ESTERS USEFUL AS SEROTONIN ANTAGONISTS

[75] Inventors: William L. Garbrecht; Gifford P. Marzoni, both of Indianapolis; Pawel Fludzinski, Zionsville, all of Ind.

[73] Assignee: Eli Lilly and Company, Indianapolis, Ind.

[21] Appl. No.: 48,166

[22] Filed: May 11, 1987

[51] Int. Cl.$^4$ .................. A61K 31/48; C07D 457/04
[52] U.S. Cl. .................................... 514/288; 546/69
[58] Field of Search ......................... 546/69; 514/288

[56] References Cited

U.S. PATENT DOCUMENTS 3,133,133  5/1964  Fairbanks ........................... 264/59
3,580,916  5/1971  Garbrecht et al. ............... 260/285.5
4,230,859  10/1980  Rucman .............................. 546/69

Primary Examiner—Donald G. Daus
Assistant Examiner—Cecilia Shen
Attorney, Agent, or Firm—Robert A. Conrad; Leroy Whitaker

[57] ABSTRACT

The present invention provides novel bicyclic ergoline esters useful as serotonin antagonists.

3 Claims, No Drawings

ERGOLINE ESTERS USEFUL AS SEROTONIN ANTAGONISTS

SUMMARY OF THE INVENTION

The present invention provides novel ergoline esters useful as serotonin antagonists. More specifically, the invention relates to a compound of the formula wherein:

R is a primary or secondary $C_1$-$C_8$ alkyl group, —$CH_2$—$C_2$—$C_4$ alkenyl, $C_3$-$C_8$ cycloalkyl, or $C_3$-$C_6$ cycloalkyl substituted with one or more primary or secondary $C_1$-$C_5$ alkyl groups, with the proviso that the total number of carbon atoms in R does not exceed 8;

$R^1$ is $C_1$-$C_4$ alkyl;

$R^2$ is $R^3$ is hydroxy, $C_1$-$C_4$ alkoxy, halo, $C_1$-$C_4$ alkyl or $$-\overset{O}{\underset{\|}{C}}-R^4;$$

$R^4$ is hydroxy, $C_1$-$C_4$ alkoxy or amino;
m is 3, 4 or 5;
n is 2, 3, 4 or 5;
p is 0, 1, 2, or 3; and
the pharmaceutically acceptable salts thereof.

The present invention also provides methods of employing, and pharmaceutical formulations containing, a compound of the invention.

DETAILED DESCRIPTION OF THE INVENTION

In the above formula, the term "primary or secondary $C_1$-$C_8$ alkyl group" represents a primary or secondary alkyl group containing from one to eight carbon atoms. Typical primary or secondary $C_1$-$C_8$ alkyl groups include methyl, ethyl, n-propyl, isopropyl, n-butyl, sec.-butyl, n-pentyl, n-hexyl, n-heptyl, iso-heptyl, n-octyl, sec-octyl and the like.

The term "—$CH_2$—$C_2$—$C_4$ alkenyl" represents groups such as allyl, crotyl, methallyl, and the like.

$C_3$-$C_8$ Cycloalkyl represents cyclopropyl, cyclobutyl, cyclopentyl, cyclohexyl, cycloheptyl and cyclooctyl.

$C_3$-$C_6$ Cycloalkyl substituted with one or more primary or secondary $C_1$-$C_5$ alkyl groups includes cyclopropylmethyl, cyclopentylmethyl, 2-cyclobutylethyl, 2-cyclohexylethyl and the like.

$C_1$-$C_4$ Alkoxy includes methoxy, ethoxy, n-propoxy, isopropoxy, n-butoxy, sec-butoxy and the like.

Halo represents fluoro, chloro, bromo and iodo.

While all of the compounds set forth above are believed useful as serotonin antagonists, the present invention does have preferred aspects. Preferably, R is a primary or secondary $C_1$-$C_8$ alkyl group, especially isopropyl. $R^1$ is preferably methyl. Further, m and n are preferably the same and either 3 or 4, while p is preferably 0 or 1.

The compounds of the present invention are prepared by esterification procedures well known to those skilled in the art. The preferred process comprises the direct coupling of a 9,10-dihydrolysergic acid derivative with an appropriately substituted bicyclic alcohol in the presence of a coupling reagent to provide the corresponding 9,10-dihydrolysergate. This reaction may be represented by the following scheme:

This reaction process necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The direct coupling of 9,10-dihydrolysergic acid and an alcohol is carried out by adding about an equimolar quantity of the alcohol starting material to a solution of the carboxylic acid in the presence of an equimolar quantity or slight excess of coupling reagent. The reaction generally is carried out in an unreactive organic solvent such as dichloromethane, tetrahydrofuran (THF) or dimethylformamide (DMF), and is typically complete within about twenty-four hours when conducted at a temperature of about 0° to about 30° C. The product is then typically isolated by filtration. The 9,10-dihydrolysergate product thus formed can be further purified, if needed, by any of several routine methods, including crystallization from common solvents, chromatography over solid supports such as silica or alumina, and related purification techniques.

The preparation of the dihydrolysergic acid derivatives which are intermediates to the compounds of the present invention is well known to those of ordinary skill in the art. According to this procedure, dihydrolysergic acid is first alkylated on the indole nitrogen with an alkyl halide in the presence of base. Liquid ammonia is a convenient solvent with sodamide as the base and an alkylating agent. An alternate alkylation procedure whereby an arylsulfonate is used in the presence of an alkali metal hydroxide is more fully described in the pending application of Marzoni, Ser. No. 782,339, filed Oct. 1, 1985. According to this procedure, an arylsulfonate of the structure R—O—SO$_2$-phenyl-Y, wherein Y is H, 4-CH$_3$, 4-Br or 4-NO$_2$ is reacted with 9,10-dihydrolysergic acid in a suitable solvent, conveniently DMSO, in the presence of base, preferably sodium or potassium hydroxide.

If the desired final product is not a 9,10-dihydrolysergic acid ester (ie; not a 1-R-6-methylergoline-8$\beta$-carboxylic acid ester), but is a 6-ethyl, 6-n-propyl, 6-n-butyl, or the like derivative, the replacement of the 6-methyl group must take place prior to the final esterification. In this procedure, it is preferable to use a lower alkyl (methyl or ethyl) ester of a 9,10-dihydrolysergic acid. Replacement of the 6-methyl group with ethyl, n-propyl, n-butyl, or the like, can be carried out by the procedure of Kornfeld and Bach, U.S. Pat. No. 4,166,182, whereby the N-methyl group is reacted with cyanogen bromide to form an N-cyano derivative. The cyano group can be removed by hydrogenation using zinc dust and hydrochloric acid. Alternatively basic hydrolysis can be used. Either procedure provides a secondary amine group at the 6-position, but also a free 8$\beta$-carboxylic acid since the hydrolysis also saponifies the 8$\beta$-lower alkyl ester group. Next, reesterification with the desired R$^2$OH alkanol is carried out followed by alkylation at N-6 using an alkyl iodide in the presence of base, conveniently in a DMF solution. This procedure is graphically illustrated by the reaction scheme.

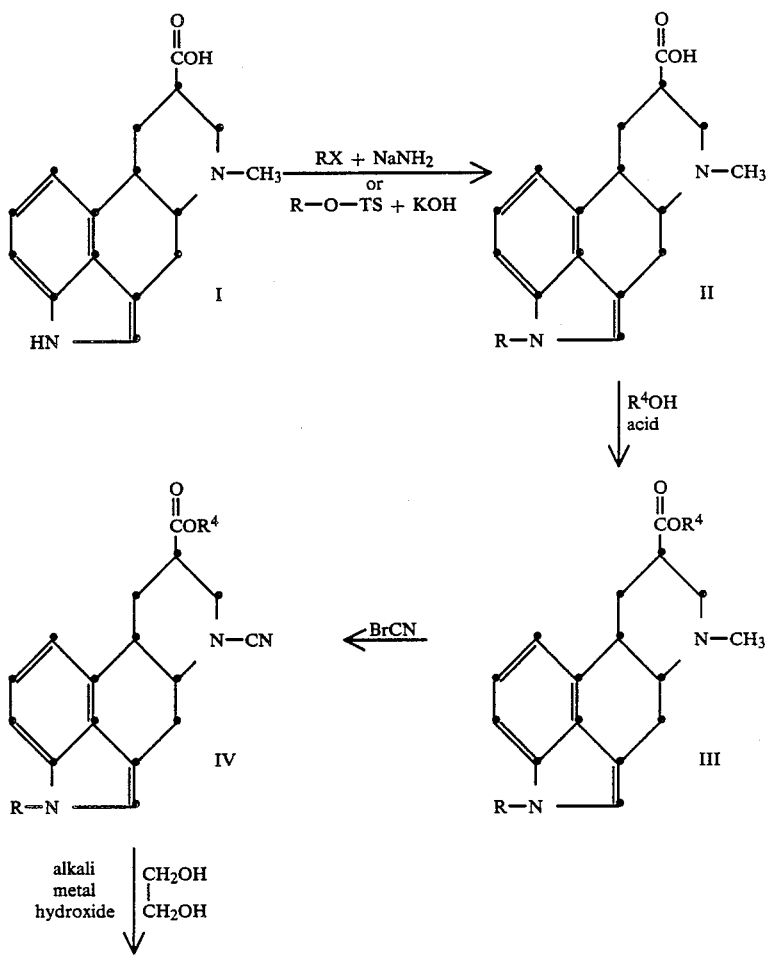

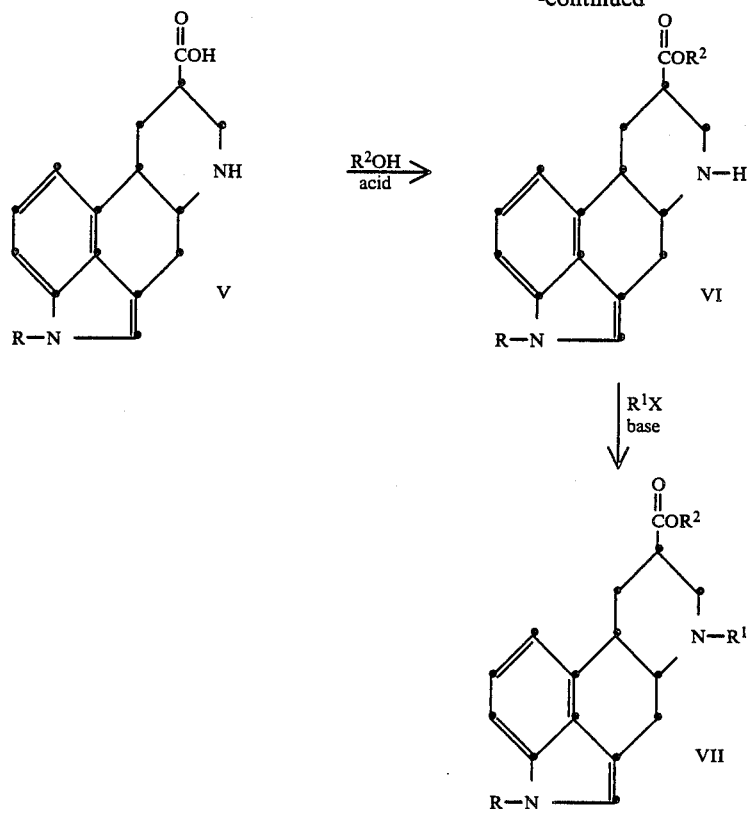

wherein R, $R^1$ and $R^2$ are as defined above, $R^4$ is $C_1$–$C_4$ alkyl and X is a good leaving group such as halo or a sulfonate derivative.

More specifically, in the above reaction scheme, 9,10-dihydrolysergic acid (I) is alkylated on the indole nitrogen with a primary or secondary $C_1$–$C_8$ alkyl halide, a $C_2$–$C_4$ alkenyl-$CH_2$ halide, a $C_3$–$C_8$ cycloalkyl halide or a $C_3$–$C_6$ cycloalkyl substituted with one or more primary or secondary $C_1$–$C_5$ alkyl groups using sodamide to create the reaction anion, or preferably using an aryl sulfonate such as a p-tosylate in the presence of potassium hydroxide in DMSO. The N-1 product (II) is then esterified with a lower alkanol $R^3OH$ (a $C_1$–$C_2$ alkanol preferably) to yield the ester (III). This intermediate is then reacted with BrCN by standard procedures to replace the methyl group and form an 6-cyano derivative (IV). Removal of the cyano group under the preferred basic conditions yields a 1-substituted-9,10-dihydro-6-desmethyllysergic acid (V), since the basic conditions also saponifies the C-8 ester group. Next, the 1-R-6-desmethyldihydrolysergic acid is re-esterified with a desired bicyclic alcohol, or a tosyl ester thereof, to yield the $N^6$-desmethyl ester (VI). The ring nitrogen at $N^6$ is then realkylated with a $C_1$–$C_4$ alkyl halide in the presence of base under standard conditions to yield the compounds of this invention (VII).

It might seem redundant to realkylate at $N^6$ with a methyl group since that group is present in the 9,10-dihydrolysergic acid starting material. However, the process would enable one to insert a "tagged" ($C^{14}$ or $H^3$) methyl group for metabolic studies.

The ergoline esters provided by this invention are amines and as such are basic in nature. Consequently, they can readily be converted to acid addition salts by reaction with organic or inorganic acids. Accordingly, an additional embodiment of this invention comprises the non-toxic pharmaceutically acceptable salts of the ergoline esters of the above formula. The particular acids utilized to form salts of this invention are not critical, and such salts include those which are prepared by reaction of the amine of this invention with any of a number of common acids such as hydrochloric, hydrobromic, sulfuric, phosphoric, nitric, perchloric, formic, acetic, butyric, citric, maleic, succinic, oxalic, fumaric, lactic, methanesulfonic, p-toluenesulfonic, and related acids. The non-toxic pharmaceutically acceptable acid addition salts which are formed by reaction of an amine of this invention with an acid such as one of the above-named acids typically exist as highly crystalline solids, and thus lend themselves to ready purification by recrystallization from common solvents such as methanol, ethanol, ethyl acetate and the like. Additionally, such salts are easily formulated for convenient administation, particularly by the oral route, to subjects in need of treatment. When desired, such acid addition salts are readily converted to the corresponding free amine base by reaction with a suitable basic compound, for instance sodium or potassium hydroxide, sodium carbonate, triethylamine, sodium bicarbonate, and the like.

The following Examples further illustrate the compounds of the present invention, and methods for their preparation. The Examples are not intended to be limiting to the scope of the invention in any respect, and should not be so construed.

EXAMPLE 1

Decahydro-5-hydroxy-1-naphthalenyl 1-isopropyl-9,10-dihydrolysergate maleate

A 25 ml three-neck round bottom flask fitted with a reflux condenser and Dean-Stark trap was charged with 2.0 g (6.4 mmol) of 1-isopropyl-9,10-dihydrolysergic acid, 2.0 g (10.5 mmol) of p-toluenesulfonic acid, 2.18 g (12.8 mmol) of 1,5-decalindiol and 25 ml of benzene. The reaction mixture was refluxed for approximately 2 hours and a thin layer chromatograph of the reaction mixture in chloroform:methanol:acetic acid (18:16:1, v:v:v) indicated that the reaction was substantially complete. The mixture was charged with 50 ml of ethyl acetate and 50 ml of water. The aqueous layer was separated and made basic with ammonium hydroxide. The aqueous layer was extracted with 50 ml of methylene chloride and the methylene chloride extract was washed with 50 ml of water. The resulting emulsion was combined with additional methylene chloride and a saturated sodium chloride solution and heated. Methanol was also added to the emulsion and the layers separated cleanly. The aqueous layer was discarded and the organic layers were combined. The solvent was evaporated from the organic phase under vacuum to provide 2.94 g of decahydro-5-hydroxy-1-naphthalenyl 1-isopropyl-9,10-dihydrolysergate.

The residue isolated above containing decahydro-5-hydroxy-1-naphthalenyl 1-isopropyl-9,10-dihydrolysergate was dissolved in 25 ml of ethanol, and the resulting solution was combined with 0.86 g (7.41 mmol) of maleic acid. To the solution was added 200 ml of diethyl ether and the desired product precipitated from solution. The mixture was cooled and the mother liquor was decanted. The resulting residue was dissolved in ethanol and the resulting solution was concentrated under vacuum. The residue was chromatographed employing high performance liquid chromatography using acetonitrile:0.1M ammonium acetate (1:1, v:v) as the eluant. The fractions containing the major component were combined and a portion of the organic solvent was evaporated under reduced pressure. The resulting aqueous solution was extracted twice with 200 ml portions of methylene chloride and the methylene chloride layers were combined. The methylene chloride phase was dried over anhydrous sodium sulfate, filtered and evaporated under vacuum. The residue was dissolved in 10 ml of ethanol and 0.08 g of maleic acid was added. To the solution was added 100 ml of diethyl ether and the crystals precipitated out of solution. The mixture was cooled in the freezer overnight and the precipitated solid was collected by vacuum filtration. The resulting solid was washed with diethyl ether and dried under vacuum to provide 180 mg of the title compound. m/e=464.

Analysis calculated for $C_{33}H_{44}N_2O_7$: Theory: C, 68.25; H, 7.64; N, 4.82; Found: C, 67.99; H, 7.74; N, 4.70.

EXAMPLE 2

Decahydro-2-naphthalenyl 1-isopropyl-9,10-dihydrolysergate maleate

To a 25 ml three-neck round bottom flask was added 2.0 g (6.4 mmol) of 1-isopropyl-9,10-dihydrolysergic acid, 2.0 g (10.5 mmol) of p-toluenesulfonic acid and 20.0 g (129.6 mmol) of decahydro-2-naphthol. The resulting mixture was heated at approximately 80° C. for 16 hours and the mixture was allowed to cool. A thin layer chromatograph of the mixture in chloroform:methanol:acetic acid (18:6:1, v:v:v) indicated that the reaction was substantially complete. The reaction mixture was charged with 100 ml of methylene chloride and 50 ml of deionized water. The pH of the mixture was adjusted to 9 with concentrated ammonium hydroxide. The organic phase was separated and washed with two 50 ml portions of deionized water. The organic phase was dried over anhydrous sodium sulfate, filtered and evaporated under vacuum to provide decahydro-2-naphthalenyl 1-isopropyl-9,10-dihydrolysergate.

The salt of the compound thus prepared was prepared as follows. To the residue was added 250 ml of diethyl ether and 0.86 g (7.41 mmol) of maleic acid. The resulting mixture was stirred for 30 minutes and cooled in the freezer. The precipitated solid was collected by vacuum filtration, washed with diethyl ether and dried. This material was dissolved in 25 ml of hot methanol and 250 ml of ether was added. The mixture was cooled in the freezer and the solid was collected by vacuum filtration. The resulting solid was vacuum dried to provide 0.67 g of the title compound. An analysis by HPLC indicated that the isolated compound was 99.8% pure.

Analysis calculated for $C_{33}H_{44}N_2O_6$: Theory: C, 70.19; H, 7.85; N, 4.96; Found: C, 70.30; H, 7.92; N, 4.95. m/e=448

$[\alpha]_{25}^D = -50.0334$

EXAMPLE 3

Octahydro-5-hydroxy-2-pentalenyl 1-isopropyl-9,10-dihydrolysergate hemihydrate

A. Octahydro-1,5-dihydroxy-2-pentalene

To a suspension of 1.99 g (14.0 mmol) of cis-bicyclo[3.3.0]octane-3,7-dione (Aldrich Chemical Co.) in 20 ml of tetrahydrofuran at a temperature of about −78° C. under a nitrogen atmosphere was added 30 ml (30 mmol) of L Selectride (Aldrich Chemical Co.) (1M in THF). The reaction mixture was allowed to warm to room temperature over a period of about 2 hours. To the mixture was added 10 ml of 1M sodium hydroxide and 10 ml of 30% hydrogen peroxide and the mixture was allowed to stir at room temperature overnight. The mixture was extracted with chloroform, and the organic extracts were combined and dried over anhydrous sodium sulfate. The solvent was evaporated under vacuum and the residue was chromatographed over silica gel employing chloroform:methanol (9:1, v:v) as the eluant. Fractions containing the major component were combined and the solvent was evaporated therefrom to provide 650 mg of octahydro-1,5-dihydroxy-2-pentalene as a white solid. mp=83°–84.5° C.

B. To a suspension of 600 mg (1.92 mmol) of 1-isopropyl-9,10-dihydrolysergic acid in 10 ml of THF was added 380 mg (2.35 mmol) of carbonyldiimidazole and the mixture was refluxed for 30 minutes until all of the reactants had gone into solution. The mixture was cooled and 260 mg (1.83 mmol) of octahydro-1,5-dihydroxy-2-pentalene was added. The reaction mixture was refluxed for 20 hours and the volatile constituents were evaporated under vacuum. The residue was dissolved in water and the resulting mixture was extracted three times with chloroform. The chloroform extracts were combined, washed twice with water and dried over anhydrous sodium sulfate. The solvent was evaporated from the mixture and the residue was chromatographed over silica gel employing chloroform:methanol (4:1, v:v) as the eluant. The fractions containing the major component were combined and the solvent was evaporated therefrom to provide 70 mg of octahydro-5-hydroxy-2-pentalenyl 1-isopropyl-9,10-dihydrolysergate hemihydrate as a solid. mp=195°-199° C.

Analysis calculated for $C_{27}H_{36}N_2O_3$: Theory: C, 72.77; H, 8.37; N, 6.29; Found: C, 72.28; H, 7.77; N, 6.20.

This invention also provides novel methods whereby 5HT$_2$ receptors are blocked. Such methods are potentially useful in treating disease states in which an excess of circulating serotonin is a major contributing cause. These disease states include hypertension, anorexia nervosa, depression, mania, carcinoid syndrome, migraine and vasospasm. The compounds of the present invention show relatively slight affinity for other receptors, such as $\alpha_1$, $\alpha_2$, $\beta$, histamine and carbachol, and thus are highly selective in their action.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to demonstrate that the compounds of the invention have an extremely high affinity for 5HT$_2$ receptors, apparent dissociation constants ($K_B$) as a measure of affinity for 5HT$_2$ receptors, expressed as the negative logarithm, have been determined according to the following procedure which was employed by Hooker, Calkins and Fleisch, *Blood Vessels*, 14, 1, (1977) for use with circular smooth muscle preparations.

Male Wistar rats, each weighing from approximately 150 g to about 300 g, were sacrificed and their external jugular veins and thoracic aortas were dissected free of connective tissue, cannulated in situ and placed in a modified Krebs' bicarbonate buffer in a suitable tissue bath. Two L-shaped 30-gauge stainless-steel hypodermic needles were inserted into each cannula and the dissected vessels gently pushed onto the needles. One needle was attached with thread to a stationary glass rod and the other to the transducer. The modified Krebs' bicarbonate buffer was composed of the following ingredients in millimoles: sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% carbon dioxide. An initial optimum resting force of 1 g and 4 g was applied to the jugular vein and aorta, respectively. Isometric contractions were recorded as changes in grams of force on a Beckman Dynograph with Statham UC-3 transducers and a microscale accessory attachment. Tissues were allowed to equilibrate 1 to 2 hours before exposure to the test compounds. Control responses to serotonin in the jugular vein and to norepinephrine in the aorta were obtained. The vessels were then incubated with appropriate concentrations of the test compound for one hour. Responses to serotinin or to norepinephrine were then repeated in the presence of the antagonist. Contraction to serotonin was evaluated in the jugular vein since this tissue is known to produce marked responses to serotonin in the absence of alpha receptors. See Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the ED$_{50}$ of the agonist in the presence of the antagonist divided by the control ED$_{50}$. These results are then expressed as the negative logarithm of $K_B$. The $-\log K_B$ values obtained for compounds of this invention are given below in Table 1 as the average of the number of trials indicated.

TABLE 1

| Example No. of Compound Tested | Serotonin Receptor Activity $-\log K_B \pm$ standard error | number of trials |
|---|---|---|
| 1 | 9.65 ± 0.21 | 4 |
| 2 | >7 | 1 |
| 3 | 9.20 ± 0.13 | 3 |

In mammals, hypertension may be mediated through 5HT$_2$ receptors. Thus, the compounds of the invention would be expected to lower blood pressure in humans as does ketanserin, another 5HT$_2$ blocker, but without the side effects attributable to alpha adrenergic receptor blockade of ketanserin.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one compound of the present invention.

Accordingly, the invention includes a pharmaceutical compositon comprising as active ingredient a compound of the invention associated with a pharmaceutically acceptable carrier, diluent or excipient therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propyl-hydroxybenzoates, talc, magnesium stearate, water, and mineral oil. The formulations can additionally include lubricating agents, wetting agents, emulsifying and suspending agents, preserving agents, sweetening agents or flavoring agents. The compositions of the invention may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, by lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only and are not intended to limit the scope of the invention. The formulations employ as active compounds any of the pharmaceutical compounds of the above formula.

Formulation 1

Hard gelatin capsules are prepared using the following ingredients:

|  | per capsule |
| --- | --- |
| decahydro-2-naphthalenyl 1-isopropyl-9,10-dihydro-lysergate maleate | 250 mg |
| starch dried | 200 mg |
| magnesium stearate | 10 mg |
| Total | 460 mg |

The above ingredients are mixed and filled into hard gelatin capsules in 460 mg quantities.

Formulation 2

Capsules each containing 20 mg of medicament are made as follows:

|  | per capsule |
| --- | --- |
| octahydro-5-hydroxy-2-pentalenyl 1-isopropyl-9,10-dihydro-lysergate hemihydrate | 20 mg |
| starch | 89 mg |
| microcrystalline cellulose | 89 mg |
| magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

Formulation 3

Capsules each containing 100 mg of active ingredient are made as follows:

|  | per capsule |
| --- | --- |
| decahydro-5-hydroxy-1-naphthalenyl 1-isopropyl-9,10-dihydrolysergate maleate | 100 mg |
| polyoxyethylenesorbitan monooleate | 50 mcg |
| starch powder | 250 mg |

The above ingredients are thoroughly mixed and are placed in an empty gelatin capsule.

Formulation 4

Tablets each containing 10 mg of active ingredient are made up as follows:

|  | per tablet |
| --- | --- |
| decahydro-2-naphthalenyl 1-isopropyl-9,10-dihydrolysergate | 10 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 5

A tablet formula is prepared using the ingredients below:

|  | per tablet |
| --- | --- |
| octahydro-5-hydroxy-2-pentalenyl 1-isopropyl-9,10-dihydrolysergate | 250 mg |
| cellulose microcrystalline | 400 mg |
| silicon dioxide fumed | 10 mg |
| stearic acid | 5 mg |
| Total | 665 mg |

The components are blended and compressed to form tablets each weighing 665 mg.

Formulation 6

Suppositories each containing 25 mg of active ingredient are made as follows:

|  | per suppository |
| --- | --- |
| decahydro-5-hydroxy-1-naphthalenyl | 25 mg |

|  | per suppository |
| --- | --- |
| 1-isopropyl-9,10-dihydrolysergate | |
| saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 5 mg of medicament per 5 ml dose are made as follows:

|  | per 5 ml of suspension |
| --- | --- |
| decahydro-2-naphthalenyl 1-isopropyl-9,10-dihydrolysergate | 5 mg |
| sodium carboxymethyl cellulose | 50 mg |
| syrup | 1.25 ml |
| benzoic acid solution | 0.10 ml |
| flavor | q.v. |
| color | q.v. |
| purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

Formulation 8

An aerosol solution is prepared containing the following components:

|  | Weight % |
| --- | --- |
| octahydro-5-hydroxy-2-pentalenyl 1-isopropyl-9,10-dihydrolysergate | 0.25 |
| ethanol | 29.75 |
| Propellant 22 (chlorodifluoromethane) | 70.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

We claim:

1. A compound of the formula

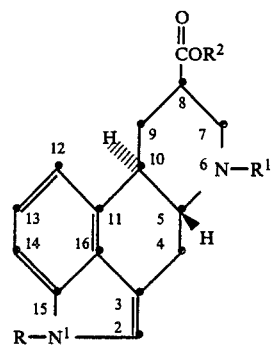

wherein:
R is a primary or secondary $C_1$–$C_8$ alkyl group, —$CH_2$—$C_2$—$C_4$ alkenyl, $C_3$–$C_8$ cycloalkyl, or $C_3$–$C_6$ cycloalkyl substituted with one or more primary or secondary $C_1$–$C_5$ alkyl groups, with the proviso that the total number of carbon atoms in R does not exceed 8;
$R^1$ is $C_1$–$C_4$ alkyl;
$R^2$ is

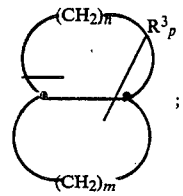

$R^3$ is hydroxy, $C_1$–$C_4$ alkoxy, halo, $C_1$–$C_4$ alkyl or

$R^4$ is hydroxy, $C_1$–$C_4$ alkoxy or amino;
m is 3 or 4;
n is 3 or 4;
p is 0, 1, or 2; and
the pharmaceutically acceptable salts thereof.

2. A method of treating hypertension which comprises administering to a hypertensive mammal a hypotensive dose of a compound of claim 1.

3. A pharmaceutical formulation for treating hypertension comprising an anti-hypertensive effective amount of a compound of claim 1 and a suitable carrier diluent, or excipient therefor.

* * * * *